US00PP08414P

United States Patent [19]

Winchel

[11] Patent Number: Plant 8,414

[45] Date of Patent: Oct. 12, 1993

[54] HYBRID TEA ROSE PLANT NAMED WEKMAR

[75] Inventor: Joseph Winchel, Harbor City, Calif.

[73] Assignee: Weeks Wholesale Rose Grower, Inc., Upland, Calif.

[21] Appl. No.: 983,464

[22] Filed: Nov. 30, 1992

[51] Int. Cl.[5] ..... A01H 5/00

[52] U.S. Cl. ..... Plt./11

[58] Field of Search ..... Plt./11, 12, 16, 17, Plt./22, 25

[56] References Cited

U.S. PATENT DOCUMENTS

P.P. 738 6/1947 Boerner ..... Plt. 11

P.P. 1,188 5/1953 Meilland ..... Plt. 11

*Primary Examiner*—Howard J. Locker

*Assistant Examiner*—E. F. McElwain

*Attorney, Agent, or Firm*—Christie, Parker & Hale

[57] ABSTRACT

A new variety of hybrid tea rose suitable for garden decoration, having flowers of an unusual bicolor combination of apricot, orange, pink and yellow coloration.

1 Drawing Sheet

BACKGROUND OF THE INVENTION

This invention relates to a new and distinct variety of hybrid tea rose. The varietal denomination of the new variety is 'Wekmar.' The plant of the new variety is bushy and upright growing. It is particularly useful for outdoor garden decoration. 'Wekmar' has as its seed parent the variety known as 'Marmalade' (U.S. Plant Pat. No. 4,243) and an unknown pollen parent.

SUMMARY OF THE INVENTION

Among the features which distinguish the new variety cv. 'Wekmar' from other presently available and known commercial rose cultivars are the following combination of characteristics: novel bicolor combination substantially as described and illustrated herein, relatively long-lived flowers of this particular color combination (4 to 5 days), and very dark foliage. Cv. 'Wekmar' may be propagated by cuttings, budding, grafting and tissue culture.

Asexual reproduction of the new variety as performed in Kern County, Calif. and Upland, Calif. by budding shows that the foregoing and other distinguishing characteristics come true to form and are established and transmitted through succeeding propagations.

COMPARISON WITH PARENT VARIETIES

The new variety may be distinguished from its seed parent, 'Marmalade,' by the following combination of characteristics: whereas 'Marmalade' has a very tall, upright habit, 'Wekmar' is significantly shorter and less severely upright in its habit; Wekmar has a dark-pigmeneted foliage with a semi-glossy finish substantially as described and illustrated herein, whereas 'Marmalade' has a significantly lighter-pigmented foliage with a very highly glossed finish; 'Wekmar' has moderately long-lived flowers that open fairly slowly, whereas 'Marmalade' produces flowers of shorter life, i.e., 2 to 3 days.

The pollen parent of the new variety is unknown.

BRIEF DESCRIPTION OF THE ILLUSTRATION

The accompanying photograph illustrates the plant in color and shows the flowering thereof from bud to full bloom depicted in color as nearly correct as it is possible to make in a color illustration of this character.

Throughout this specification, color values are those set forth in the Colour Chart of The Royal Horticultural Society of London, England, except where common terms of color definition are employed.

DESCRIPTION OF THE NEW VARIETY

The following descriptive matter pertains to plants of the new cultivar grown outdoors in August, 1992 in Upland, Calif. Phenotypic expression may vary with differences in conditions of light, soil and climate.

FLOWERING HABIT

The new variety usually bears its flowers singly, sometimes with two to three or more per stem in rounded clusters, on stems which are strong and of medium length for the class. Outdoors the plant blooms very freely and nearly continuously during the growing season. The flowers have a slight tea to fruity fragrance.

BUD

The peduncle is of short to average length for the class, of average to heavy caliper, and usually erect and stiff. It is moderately smooth with some stipitate glands. Peduncle color is between 144A and 147A, sometimes blushed on the side facing the sun with near 176A.

Before the calyx breaks, the bud is of medium to large size for the class, medium in length, and pointed to ovoid in shape. The surface of the bud bears some stipitate glands and hairs, usually with slender foliaceous parts extending beyond the tip of the bud is equal to one-half or more of its length. Bud color is between 146B and 138A.

The inner surface of the sepals is covered with fine woolly tomentum; sepal margins bear some slender foliaceous parts, some stipitate glands and hairs.

As the first petals open, the bud is somewhat large for the class, of medium length, and moderately pointed to ovoid in form. The color of the outside surfaces of the newly opened petals is between 12C and 16D. The color of the inside surfaces of the newly opened petals is between 40C and 34B with a medium-sized basal attachment zone with coloration of between 12B and 8A. The bud opens well and is not prevented from opening by cold, hot or dry weather.

BLOOM

When fully open, the bloom is moderately large for the class, ranging from 11 to 14 cm. in diameter. Petalage is double with 28 to 32 petals and 1 to 4 petaloids arranged regularly. When partially open, the bloom form is moderately cupped to high-centered and the petals are somewhat tightly spiraled to undulated with petal edges moderately rolled outward. When fully open, the flower form is somewhat more cupped to full, and the petals are more loosely cupped to undulated with petal edges more rolled to reflexed outward.

PETALS

The petals are of somewhat heavy substance and of moderate thickness, with inside surfaces slightly shiny to satiny and outside surfaces moderately shiny. The outside petals are nearly round to broadly obovate in shape with apices mostly rounded to flat. The inside petals are broadly ovate to obovate in shape with apices somewhat rounded to flat.

NEWLY OPENED FLOWER

The outside surface of the outer, intermediate and inner petals is between 12C and 16D. The inside surface of the outer, intermediate and inner petals is between 40D and 34D with a medium-sized basal attachment zone with coloration of between 12B and 8A.

The general tonality of the newly opened flower is between 40D and 34D with a reverse of between 12C and 16D.

THREE-DAY-OLD FLOWER

The outside surface of the outer and inner petals is between 11D and 18C. The inside surface of the outer and inner petals is between 43D and 35C with a medium-sized basal attachment zone with coloration of between 11C and 8D.

The general tonality of the three-day-old flower is between 43D and 35C with a reverse of between 11D and 18C.

On the spent bloom, the petals usually drop off cleanly and are not particularly affected by cold, hot or dry weather.

In August, blooms on the bush growing in the garden generally last four to five or more days. Cut roses grown outdoors and kept at normal indoor room temperatures generally last from four to five or more days.

REPRODUCTIVE ORGANS

Stamens are many in number and are arranged regularly about the pistils; a few are mixed with the petaloids. The filaments are somewhat short to medium in length, most with anthers. The anthers are moderately large for the class and all open approximately at the same time. Anther color is near 16B when immature and near 166B at maturity. Pollen is very abundant and near 12D in color.

Pistils are average to many in number (approximately 60). The styles are moderately uneven, somewhat short to average in length, moderately thin to average in caliper, and somewhat loosely bunched. Stigma and style color is near 10C. Ovaries are usually enclosed in the calyx.

Hips are moderately short to average in length, somewhat flat and globular in form, and near 25B in color when ripe. The hip surface is very smooth with somewhat thick fleshy walls. The sepals fall away soon. Seeds are few to average in number (approximately 8 to 15), and moderately large in size.

FOLIAGE

The compound leaves are usually comprised of three, five and seven leaflets and are borne abundantly. The leaves are medium-sized for the class, moderately heavy in texture, and moderately semi-glossy to matte in finish. The leaflets are shaped very oval with moderately acute to mucronate apices and somewhat round to acute bases. Their margins are usually simply serrate to slightly irregular.

The upper surface of the mature leaf is between 147A and 137A. The under surface of the mature leaf is between 147D and 138C. The upper and under surface of the young leaf is between 147B and 138A, often heavily suffused with between 176A and 183A.

The rachis is somewhat heavy in caliper and very grooved with some hairs and stipitate glands on the edges of the upper side. The under side of the rachis is moderately smooth with few stipitate glands and small prickles.

The stipules are moderately short to medium in length with somewhat narrow to medium width, and points that sometimes turn out an an angle of less than 45 degrees.

The plant displays an above-average degree of resistance to powdery mildew as compared to other commercial varieties grown under comparable conditions in Upland, Calif.

GROWTH

The plant's growing habit is bushy, upright and medium to tall with moderately full branching. 'Wekmar' displays very vigorous growth and the canes are of somewhat heavy caliper for the class.

The color of the major stems is between 152B and 160A. They bear some large prickles which are moderately long for the class. The large prickles are almost straight, angled moderately downward with a medium length and somewhat narrow base; prickle color is near 165B. The major stem bears no small prickles and no hairs.

The color of the branches is between 146B and 147B. They bear several large prickles which are moderately long for the class. The large prickles are almost straight, angled moderately downward with a medium length and somewhat narrow base; prickle color is near 160A. The branches bear a few small prickles of similar coloration. There are no fine hairs.

The color of the new shoots is near 144B, sometimes suffused with between 176A and 183A. They bear several large prickles which are moderately long for the class. The large prickles are almost straight, angled moderately downward and with a medium length and somewhat narrow base; prickle color is of similar coloration as the new shoots. The shoots bear several small prickles, also of similar coloration. There are no fine hairs.

I claim:

1. A new and distinct variety of hybrid tea rose plant substantially as described and illustrated herein.

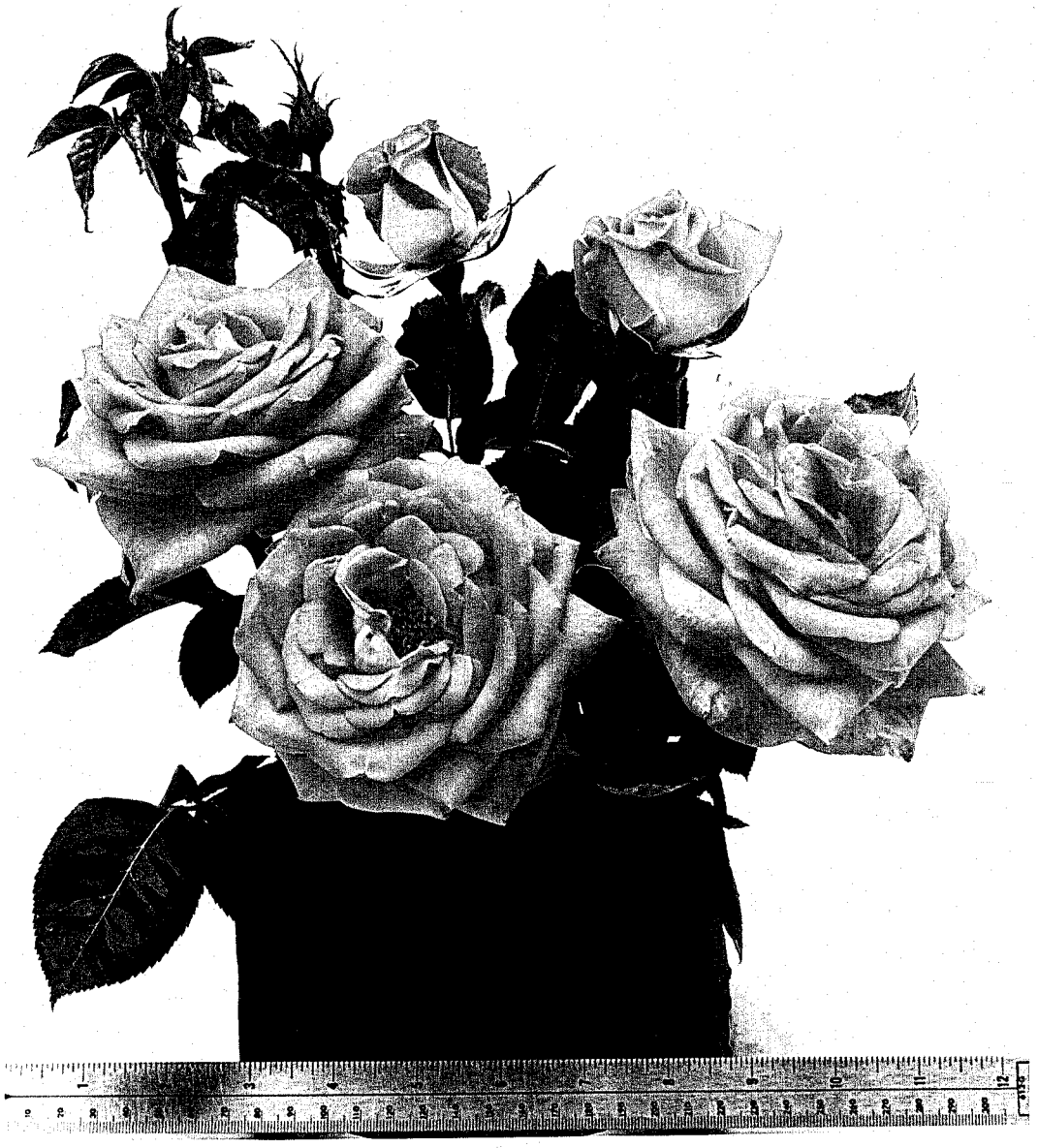

* * * * *